(12) United States Patent
Towner et al.

(10) Patent No.: US 9,474,748 B2
(45) Date of Patent: Oct. 25, 2016

(54) ADJUVANT CHEMOTHERAPY FOR ANAPLASTIC GLIOMAS

(71) Applicant: OKLAHOMA MEDICAL RESEARCH FOUNDATION, Oklahoma City, OK (US)

(72) Inventors: Rheal A. Towner, Piedmont, OK (US); Robert A. Floyd, Oklahoma City, OK (US)

(73) Assignee: OKLAHOMA MEDICAL RESEARCH FOUNDATION, Oklahoma City, OK (US)

( * ) Notice: Subject to any disclaimer, the term of this patent is extended or adjusted under 35 U.S.C. 154(b) by 98 days.

(21) Appl. No.: 14/159,753

(22) Filed: Jan. 21, 2014

(65) Prior Publication Data

US 2014/0200234 A1    Jul. 17, 2014

Related U.S. Application Data

(63) Continuation of application No. 12/552,792, filed on Sep. 2, 2009, now Pat. No. 8,633,249.

(60) Provisional application No. 61/093,661, filed on Sep. 2, 2008.

(51) Int. Cl.
| | |
|---|---|
| *A61K 31/15* | (2006.01) |
| *A61K 31/185* | (2006.01) |
| *A61K 31/4748* | (2006.01) |
| *A23L 1/30* | (2006.01) |
| *A61K 45/06* | (2006.01) |
| *A61K 31/166* | (2006.01) |
| *A61K 31/175* | (2006.01) |

(52) U.S. Cl.
CPC .............. *A61K 31/4748* (2013.01); *A23L 1/30* (2013.01); *A61K 31/15* (2013.01); *A61K 31/166* (2013.01); *A61K 31/175* (2013.01); *A61K 31/185* (2013.01); *A61K 45/06* (2013.01)

(58) Field of Classification Search
CPC ............................ A61K 31/185; A61K 31/15
See application file for complete search history.

(56) References Cited

U.S. PATENT DOCUMENTS

| | | | |
|---|---|---|---|
| 5,488,145 | A | 1/1996 | Carney |
| 5,569,902 | A | 10/1996 | Wood et al. |
| 2007/0032453 | A1 | 2/2007 | Towner et al. |
| 2009/0325893 | A1 | 12/2009 | Garland et al. |

FOREIGN PATENT DOCUMENTS

| | | |
|---|---|---|
| WO | WO 95/17876 | 7/1995 |
| WO | WO 01/74349 | 10/2001 |
| WO | WO 2007/019065 | 2/2007 |

OTHER PUBLICATIONS

Cao et al., "Use of magnetic resonance imaging to assess blood-brain/blood-glioma barrier opening during conformal radiotherapy," *J. Clin. Oncol.*, 23:4127-36, 2005.

Culot et al., "Cerebrovascular protection as a possible mechanism for the protective effects of NXY-059 in preclinical models: An in vitro study," *Brain Res.*, 1294:144-152, 2009.

Dehouck et al., "In vitro blood-brain barrier permeability and cerebaral endothelial cell uptake of the neuroprotective nitrone compound NXY-059 in normoxic, hypoxic and ischemic conditions," *Brain Res.*, 955:229-235, 2002.

Doblas et al., "Phenyl-tert-butylnitrone induces tumor regression and decreases angiogenesis in a C6 rat glioma model," *Free Radic. Biol. Med.*, 44(1):63-72, 2008.

Floyd et al., "Nitrones as therapeutics," *Free Radical Biology & Medicine*, 45(10):1361-74, 2008.

Garteiser et al., "5493: Antitumor effects by novel nitrone compound OKN007 in a rat C glioma model," *Proceedings of the American Association for Cancer Research Annual Meeting*, 50:1324, 2009.

Ginsberg, "Life after cerovive: A personal perspective on ischemic neuroprotection in the post-NXY-059 era," *Stroke*, 38(6):1967-1972, 2007.

Kuroda et al., "Neuroprotective effects of a novel nitrone, NXY-059, after transient focal cerebral ischemia in the rat," *J Cereb Blood Flow Metab.*, 19(7):778-787, 1999.

Maples et al., "Nitrone-related therapeutics: Potential of NXY-059 for the treatment of acute ischaemic stroke," *CNS Drugs*, 18(15):1071-1084, 2004.

Office Communication issued in Australian Patent Application No. 2009288057, dated Oct. 11, 2013.

Office Communication issued in U.S. Appl. No. 12/552,792, dated Aug. 23, 2013.

Office Communication issued in U.S. Appl. No. 12/552,792, dated Feb. 27, 2013.

Office Communication issued in U.S. Appl. No. 12/552,792, dated Nov. 6, 2012.

Office Communication issued in U.S. Appl. No. 12/552,792, dated May 4, 2012.

Office Communication issued in U.S. Appl. No. 12/552,792, dated Jan. 12, 2012.

PCT International Search Report and Written Opinion, issued in International Application No. PCT/US2009/055749, date of mailing: Dec. 8, 2009.

(Continued)

*Primary Examiner* — Samira Jean-Louis
(74) *Attorney, Agent, or Firm* — Parker Highlander PLLC

(57) ABSTRACT

The present invention involves the use of 2,4-disulfonyl phenyl tert-butyl nitrone (2,4-ds-PBN) in the treatment and prevention of gliomas. The 2,4-ds-PBN may be used alone or combined with other traditional chemo- and radiotherapies and surgery, to treat or prevent glioma occurrence, recurrence, spread, growth, metastasis, or vascularization.

12 Claims, 6 Drawing Sheets

(56) References Cited

OTHER PUBLICATIONS

Shuaib et al., "NXY-059 for the treatment of acute ischemic stroke," *N. Engl. J. Med.*, 357:562-71, 2007.

Wang and Shuaib, "Neuroprotective effects of free radical scavengers in stroke," *Drugs Aging*, 24:537-46, 2007.

Watanabe et al., "244: Mechanistic study on the anti-tumor effects by novel nitrone compound OKN007 in a rat C6 glioma model and cultured C6 cells," *Free Radical Biology & Medicine*, 45(Suppl. 1):S92, 2008.

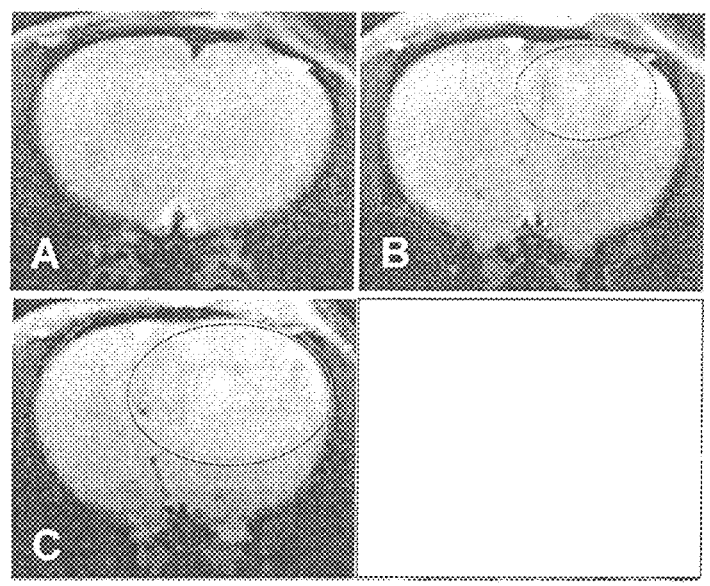
FIG. 1A-C

R = H,     N-tert-butyl nitrone (PBN)
R' = -SO₃Na   2-sulfonyl PBN (2-S-PBN)
R,R' = -SO₃Na 2,4-disulfonyl PBN (OKN007)

ADJUVANT CHEMOTHERAPY FOR ANAPLASTIC GLIOMAS

This application is a continuation application of U.S. patent application Ser. No. 12/552,792, filed Sep. 2, 2009, now U.S. Pat. No. 8,633,249, issued Jan. 21, 2014, which claims benefit of priority to U.S. Provisional Patent Application Ser. No. 61/093,661, filed Sep. 2, 2008. The entire text of each of the above referenced disclosures is specifically incorporated herein by reference.

BACKGROUND OF THE INVENTION

1. Field of the Invention

The present invention relates generally to the fields of oncology and chemotherapy. More particularly, it concerns the use of 2,4-disulfonyl phenyl tert-butyl nitrone (2,4-ds-PBN), alone or in combination with chemo- or radiotherapy, to treat gliomas.

2. Description of Related Art

Gliomas are a diverse group of brain tumors that arise from normal "glial" cells of the brain and/or their precursor cells. The most important determinant of survival for gliomas is the "grade" of the glioma. Secondary determinants of survival are age at diagnosis, performance status, and extent of surgery. Patients with low-grade gliomas have a protracted natural history with generally long survival times, while those with high grade gliomas are much more difficult to successfully treat and have shorter survival times. All gliomas have specific signs and symptoms that are primarily related to the location and size of the glioma.

The temporal lobe gliomas, for example, may cause seizures, difficulty with speech and/or loss of memory. The frontal lobe gliomas may cause seizures, behavioral changes, weakness of the arms or legs on the opposite side of the body, and/or difficulty with speech. The occipital gliomas may cause loss of vision. The parietal gliomas may cause loss of spatial orientation, diminished sensation on the opposite side of the body, and/or inability to recognize once familiar objects or persons.

Astrocytomas are glioma tumors that arise from brain cells called astrocytes or their precursors. Astrocytes are cells in the central nervous system that support neuronal function. Astrocytomas can be graded by histologic features that signify increasing malignancy into astrocytoma, anaplastic astrocytoma, or glioblastoma multiforme. Anaplastic astrocytoma and glioblastoma multiforme are considered high-grade gliomas while the astrocytoma is considered to be a low-grade glioma. High-grade tumors grow rapidly and can easily infiltrate and spread through the brain. Low-grade astrocytomas can also infiltrate the brain but are usually more localized and grow slowly over a long period of time. High-grade tumors are much more aggressive and require very intense therapy. The majority of astrocytic tumors in children are low-grade, whereas the majority in adults are high-grade. Astrocytomas can occur anywhere in the brain and spinal cord, however the majority are located in the cerebral hemispheres.

Oligodendrogliomas are also gliomas. They arise from oligodendrocytes and/or their cell precursors. Normal oligodendrocytes provide myelin, a fatty substance that covers nerve axons in the brain and spinal cord and allows nerves to conduct electrical impulses more efficiently. Oligodendrogliomas are classified as low grade oligodendroglioma (less aggressive) and anaplastic oligodendroglioma (more aggressive). More common than pure oligodendrogliomas are low grade and anaplastic tumors that are a mixture of astrocytoma and oligodendroglioma ("oligoastrocytomas").

Anaplastic oligodendrogliomas and mixed oligoastrocytomas are more sensitive to cytotoxic chemotherapy than astrocytomas. A high rate of response to the PCV (procarbazine (matulane), CCNU (lomustine), vincristine) chemotherapy has made the use of this regimen, if not the standard of care for these tumors, at least a very common treatment. Low grade oligodendrogliomas are also sensitive to chemotherapy, and PCV can be used when low grade tumors begin to grow despite prior surgery/radiation therapy.

In 1983, it was reported that surgery plus radiation therapy and BCNU chemotherapy significantly improved the survival of patients with malignant glioma, as compared to those treated with surgery plus radiation therapy without chemotherapy. In one study, both procarbazine and streptozotocin demonstrated effectiveness similar to that of BCNU. Other studies showed that BCNU alone is as effective as BCNU followed by procarbazine, and that PCNU was no better than BCNU. In some studies the PCV combination was found superior to BCNU for anaplastic gliomas, while in other studies they are considered equivalent.

Another approach involves the combined use of DFMO-PCV in treating anaplastic gliomas, extending the study of Levin et al. (2000). Surprisingly, and in marked contrast to the results seen with glioblastoma multiforme, the combination of DFMO and PCV significantly increased the overall survival of patients with anaplastic gliomas. It is possible that a feature distinguishing tumor response to DFMO is the level and activity of the enzyme ornithine decarboxylase (ODC). It is likely that one factor that distinguishes DFMO benefit is the tumor level of ODC; patients with relatively lower levels of ODC appear to respond better to DFMO and DFMO-nitrosourea combinations. This conclusion is based on published observations that show that (1) ODC levels are directly correlated with malignant grade of glioma (Scalabrino et al., 1982; Scalabrino an Ferioli, 1985; Ernestus et al., 1992; 1996); (2) the fact that DFMO (+/− methylglyoxal bisguanylhydrazone) activity was not seen in glioblastoma multiforme and best seen in mid-grade anaplastic gliomas (Levin et al., 1992; 1995) with lower ODC levels; and (3) in combination with a nitrosourea, activity was not seen in glioblastoma multiforme and best seen in mid-grade anaplastic gliomas (Prados et al., 1989; Levin et al., 2000) with lower ODC levels.

The inventors have demonstrated the efficiency of phenyl-tert-butyl-nitrone (PBN) as a potential anti-glioma drug in the pre-treatment of a rat C6 glioma implantation model (Doblas et al., 2008). MR results from untreated rats showed the diffusive invasiveness of C6 gliomas, with some associated angiogenesis. PBN administration as a pretreatment was found to clearly induce a decrease in growth rate and tumor regression as well as preventing angiogenesis. However, post-treatment of PBN had little effect for tumor regression compared with pre-treatment. MR findings rivaled those from histology and angiogenesis marker immunostaining evaluations.

In addition to controlled survival-based clinical trials, a large number of other agents have been tested in response-based studies in glioma patients. Regardless, there is a need for effective and improved therapies for anaplastic gliomas.

SUMMARY OF THE INVENTION

Thus, in accordance with the present invention, there is provided a method for treating a glioma in a subject comprising administering to said subject with glioma a dose of 2,4-disulfonyl derivative of phenyl-tert-butyl nitrone effective to inhibit the growth of said glioma. The method human subject may have a recurrent or metastatic glioma, or have previously failed one or more anti-glioma therapies. The effective dose may be from about 5 to about 150 mg/kg body weight per day. Administering may be through dietary administration, such as through supplementation of a food component. The effective amount is from about 0.005 w/w % to about 0.1 w/w % of the diet being administered. The glioma may be an astrocytoma, an oligodendroglioma, or a glioblastoma multiforme. The method may also further comprise a secondary anti-glioma therapy, such as chemotherapy, including is lomustine, vincristine, matulane, PCV, BCNU, CCNU and/or DFMO, radiation or surgery. Treating may comprise inhibiting the vascularization, growth or spread of a glioma, reducing tumor burden, or preventing metastasis. The subject may be an non-human animal subject or a human.

In another embodiment, there is provided a method for inhibiting glioma development comprising (a) identifying a subject at risk of developing a glioma and (b) administering to said subject a dose of 2,4-disulfonyl derivative of PBN or phenyl-tert-butyl nitrone effective to inhibit the development of said glioma. The subject may have a familial history of cancer or may have been exposed to a carcinogenic environment. Specific glioma risk factors include exposure to N-nitroso compounds or X-irradiation. The effective dose is from about 5 to about 150 mg/kg body weight per day. Administering may be through dietary administration, such as through supplementation of a food component, oral administration in the form of a pill or in liquid form, or via intravenous injection. The effective amount may be from about 0.005 w/w % to about 0.1 w/w % of the diet being administered. The glioma may be an astrocytoma, an oligodendroglioma, or a glioblastoma multiforme. The subject may be a non-human animal subject or a human.

In yet another embodiment, there is provided a method for inhibiting glioma recurrence comprising administering to a subject previously having a glioma a dose of 2,4-disulfonyl derivative of PBN or phenyl-tert-butyl nitrone effective to inhibit the development of said glioma. The glioma may be an astrocytoma, an oligodendroglioma, or a glioblastoma multiforme. The effective dose may be from about 5 to about 150 mg/kg body weight per day. Administering may be through dietary administration, such as through supplementation of a food component, oral administration in the form of a pill or in liquid form, or via intravenous injection. The effective amount is from about 0.005 w/w % to about 0.1 w/w % of the diet being administered. The subject may be an non-human animal subject or a human. The method may further comprise administering a second agent that inhibits glioma occurrence. The method may also further comprise screening for glioma formation in said subject.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or a method that "comprises," "has," "contains," or "includes" one or more elements possesses those one or more elements, but is not limited to possessing only those one or more elements or steps. Likewise, an element of a device or method that "comprises," "has," "contains," or "includes" one or more features possesses those one or more features, but is not limited to possessing only those one or more features.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-C: MRI (T1-weighted axial slice in mid-brain region) of C6 glioma at days 10 (FIG. 1A), 15 (FIG. 1B) and 18 (FIG. 1C) after cell injection. Note tumor outlined by arrows.

FIG. 2-1(a)-2-2(d): H&E staining (1) and von Willebrand factor immunostaining (2) of a C6 glioma at 23 days. Areas of normal tissue (×40; a), glioma (×40; b), necrosis (×40; c) and infiltration (×10; d) are presented (Doblas et al., 2008).

DESCRIPTION OF ILLUSTRATIVE EMBODIMENTS

1. The Present Invention

Figures 1A, 2, 2D:
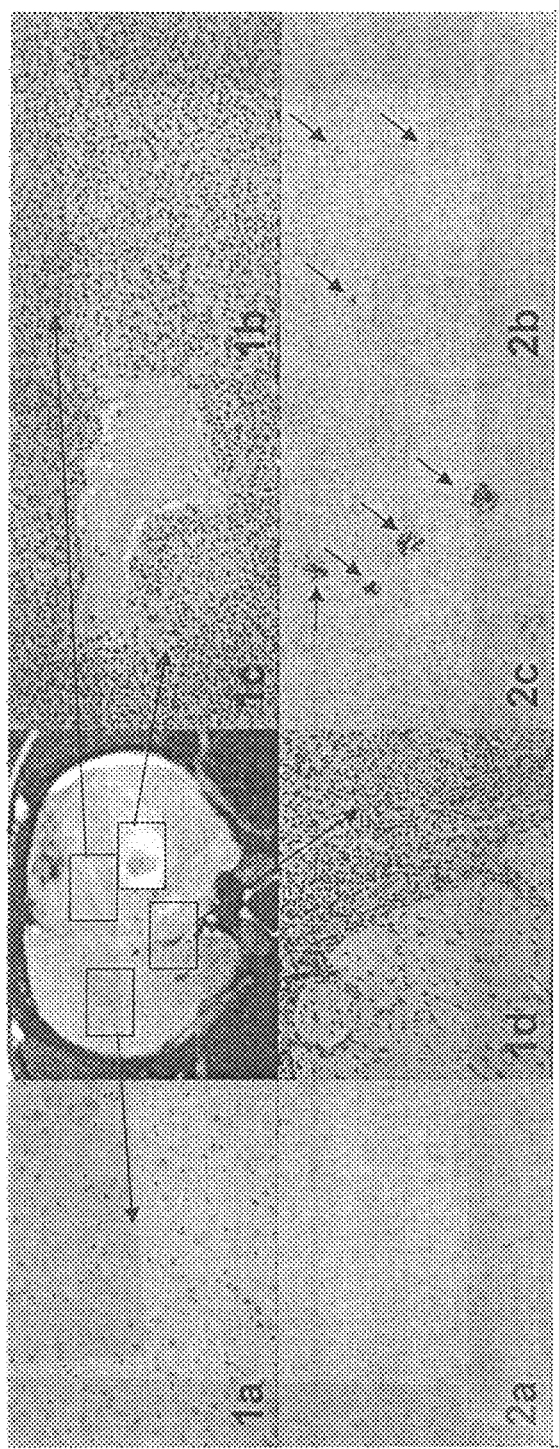
Figure 3:
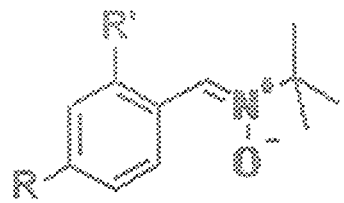
FIG. 3: Parent nitrone, PBN, and sulfonyl derivatives, 2-S-PBN and 2,4-ds-PBN.

The prognosis of patients who are diagnosed with glioblastoma multiforme is very poor, due to the difficulty of an early and accurate diagnosis and the lack of currently efficient therapeutic compounds. Using a glioma model previously applied to the testing of PBNs and non-sulfonyl derivatives thereof, the inventors examined the effect of a nitrone compound, 2,4-ds-PBN that is a structural analog of PBN. Magnetic resonance results from 2,4-ds-PBN post-treated rats indicated apparent decrease in tumor volume and the delay in tumor growth rate. 2,4-ds-PBN post-treatment was also significantly effective in increasing survival rate.

This result was somewhat unexpected and surprising as sulfonated derivatives of PBN are known not to be able to readily cross the blood-brain-barrier (BBB). PBN, the parent nitrone, has been previously found to easily penetrate the BBB (Wang & Shuaib, 2007). 2,4-disulfonyl PBN (2,4-ds-PBN) is structurally related to the parent compound PBN, but contains two sulfonyl groups that make it much more water-soluble. As a result of the increased water solubility 2,4-disulfonyl PBN cannot easily pass through the BBB, as compared to PBN (Wang & Shuaib, 2007). Ideally, drugs that are to be used as anti-glioma therapy need to pass the endothelial junctions of the BBB to reach the majority of tumor cells (Cao et al., 2005). It is possible that malignant gliomas have acquired the ability to actively degrade tight junctions by secreting soluble factors, eventually leading to BBB disruption within invaded brain tissue (Schneider et al., 2004). Regardless, it has never been thought that 2,4-disulfonyl PBN would reach sufficient amounts in glioma tissue to have any therapeutic effect. For instance Renovis Pharmaceuticals, administered 2,4-disulfonyl PBN as an anti-stroke therapeutic agent via i.v. administration to concentrate this compound into brain tissue (Shuaib et al., 2007).

These and other aspects of the invention are described in detail below.

2. Anaplastic Glioma Strata

A. Clinical Features

The anaplastic gliomas are intermediate grade infiltrative gliomas—classified between low (localized, slow growing) and glioblastoma multiforme (rapidly growing and highly invasive). Anaplastic astrocytomas (AA) are tumors that arise from brain cells called astrocytes and/or their precursors. Astrocytes are support cells of the central nervous system. The majority of astrocytic tumors in children are low-grade, whereas the majority in adults are high-grade. These tumors can occur anywhere in the brain and spinal cord.

Oligodendrogliomas are gliomas derived from oligodendrocytes and/or their precursors. Oligodendrocytes that have a role in the structure and function of myelinated neurons in the brain. Anaplastic oligodendroglioma (AO) are more aggressive than oligodendrogliomas, but are also more sensitive to chemotherapy than are anaplastic astrocytomas. A high rate of response to the use of PCV (procarbazine, CCNU, vincristine) chemotherapy has led to the common use of PCV chemotherapy prior to radiation therapy, following irradiation, and/or at tumor recurrence and progression. Another glioma appears as histologic mixture of both oligodendroglioma and astrocytoma tumor forms and is called oligoastrocytoma. While oligoastrocytoma can be low-grade, the majority of the mixed oligoastrocytomas are anaplastic oligoastrocytomas (AOA).

The last glioma subgroup are ependymomas. One subtype of malignant ependymomas is the anaplastic ependymoma (AE); these tumors arise from ependymal cells and/or their precursors that line the cerebrospinal fluid passageways, called ventricles. These tumors are classified as either supratentorial (in the top part of the head) or infratentorial (in the back of the head).

Clinical features and symptoms produced by gliomas depend on the location of the tumor and the age of the patient. The most common location for gliomas is in the cerebral hemispheres in adults and the cerebellum, brainstem, hypothalamus, and thalamus in children. Spinal cord gliomas are much less common then gliomas of the brain. Patients with these tumors have symptoms that vary depending on location in the brain or spinal cord. They can produce symptoms of headache, seizures, nausea and vomiting, limb weakness, unilateral sensory changes, personality change, and unsteadiness in walking.

B. Classifications

Anaplastic Astrocytoma. The histologic features of anaplastic astrocytomas are similar to those of low-grade astrocytomas but these features are more abundant and exaggerated. These tumors are WHO grade III (Kleihues et al., 1993; Kleihues and Cavenee, 2000). Cellularity is more increased, as are nuclear and cellular pleomorphism. These features may be extreme, with back-to-back cells and bizarre, hyperchromatic nuclei. Cytoplasm may be scanty, with nuclear lobation and enlargement indicating anaplasia. Mitotic activity is easily recognized in most anaplastic astrocytomas but inexplicably may be absent in areas with gemistocytes.

The range of anaplasia in this grade is broad, with some examples showing low cellularity and pleomorphism with a few mitotic figures and others being highly cellular and pleomorphic with frequent mitoses, lacking only the necrosis required for a histologic diagnosis of glioblastoma. For this reason, it is useful to have a more objective indicator of behavior, and some markers of cell proliferation have been used in an attempt to predict prognosis more accurately. The most used markers in this area have been antibodies to bromodeoxyuridine (BrdU) and Ki-67 (Davis et al., 1995). The cellular incorporation of BrdU is a specific marker of the DNA synthesis phase of the cell cycle, whereas the Ki-67 antibody labels an antigen that is present in all phases of the cell cycle except $G_0$. Both antibodies can be identified by immunohistochemical staining in paraffin-embedded tissue sections. As a generalization, higher labeling rates for anaplastic astrocytomas is associated with poor prognosis (Hoshino et al., 1993; Davis et al., 1995; Lamborn et al., 1999).

Glioblastoma multiforme. Glioblastoma, also known as glioblastoma multiforme, is the glioma with the highest grade of malignancy, WHO grade IV (Kleihues and Cavenee, 2000). It represents 15% to 23% of intracranial tumors and about 50%-60% of astrocytomas. Most examples are generally considered to arise from astrocytes because glial fibrillary acidic protein can be identified in the cell cytoplasm. Some examples, however, apparently arise from other glial lineages, such as oligodendrocytes. Glioblastoma is the most frequently occurring astrocytoma. Autopsy and serial biopsy studies have shown that some astrocytomas progress through the grades of malignancy with transformation from low-grade to anaplastic astrocytoma to glioblastoma (Muller et al., 1977). But, because some examples of glioblastoma appear to arise rapidly in otherwise normal patients and are recognized when they are small, it is thought that this variety of glioblastoma can also arise directly from malignant transformation of astrocyte precursor cells without passing through the lower grades of malignancy (Kleihues and Ohgaki, 1997; 1999).

Tumor necrosis is the characteristic gross feature that distinguishes glioblastoma from anaplastic astrocytoma (Nelson et al., 1983; Burger et al., 1985; 1991). Another microscopic feature that is distinctive and diagnostic is the presence of proliferative vascular changes within the tumor. These changes may occur in the endothelial cells (vascular endothelial hyperplasia or proliferation) or in the cells of the vessel wall itself (vascular mural cell proliferation). Both types of change are sometimes considered together as microvascular proliferation. Glioblastomas cellularity is usually extremely high. The individual cells may be small, with a high nuclear:cytoplasmic ratio, or very large and bizarre, with abundant eosinophilic cytoplasm. These same small cells may appear to condense in rows around areas of tumor necrosis, forming the characteristic pseudopalisades. Glioblastoma tumors have a propensity to infiltrate the brain extensively, spreading even to distant locations and giving the appearance of a multifocal glioma. Some examples are truly multifocal (i.e., arising in multiple simultaneous primary sites) while many of these multifocal tumors show a histologic connection when the whole brain is examined at autopsy.

Oligodendrogliomas. Like astrocytomas, oligodendrogliomas mimic the histology of their presumed cell of origin. They also arise primarily in the white matter but tend to infiltrate the cerebral cortex more than do astrocytomas of a similar grade of malignancy. Like astrocytomas, grading schemes of histologic malignancy have been used for oligodendrogliomas, but these correlate less well with prognosis than those used for astrocytomas (Burger et al., 1987; Bigner et al., 1998; Daumas-Duport et al., 1997). Many of the histologic features used to grade oligodendrogliomas are similar to those used for astrocytomas: cellularity, pleomorphism, mitotic activity, vascular changes, and necrosis. Lower-grade oligodendrogliomas may have microcysts. Oligodendrogliomas of all histologic grades tend to infiltrate the cortex readily and to form clusters of neoplastic cells in the subpial region, around neurons, and around blood vessels. In general, the cells of oligodendrogliomas have round, regular nuclei and distinct cytoplasmic borders with clearing of the cytoplasm. Another fairly distinctive and diagnostically helpful feature is the vascular pattern of oligodendrogliomas, referred to as "chicken-wire" vessels that can divide the tumor into discrete lobules. With increasing anaplasia, oligodendrogliomas can become highly cellular and pleomorphic, approaching an appearance of glioblastoma multiforme with the presence of necrosis. Although it is correct to classify these as anaplastic oligodendrogliomas, some would use the term glioblastoma once necrosis is identified in any high-grade glial neoplasm. One justification for separating anaplastic oliogdendrogliomas from astrocytic glioblastomas is the slightly better prognosis of the former, even in this highest grade of malignancy. Some authors have reported that a MIB-1 labeling index of >3%-5% predicts a worse prognosis in oligodendrogliomas (Heegard et al., 1995; Kros et al., 1996; Dehghani et al., 1998).

Oligoastrocytomas. Many, if not most, oligodendrogliomas occur with a regional or intimate cellular mixture of astrocytoma. For the diagnosis of mixed glioma, the proportion of each should be substantial, but authors have differing opinions with respect to exact numbers; usually a mixture with a range from 10% to 25% of the minor element is used to diagnose a mixed glioma. Oligoastrocytomas and anaplastic oligoastrocytomas correspond to WHO grade II or grade III, respectively (Kleihues and Cavenee, 2000). Histologic features of anaplasia may be present in either component and will affect the prognosis adversely. Such features include marked cellular pleomorphism, high cellularity, and a high mitotic rate. Microvascular proliferation and necrosis may also be seen. Prognosis and response to therapy have not been shown to depend on the proportion of the oligodendroglial versus the astrocytic component (Shaw et al., 1994), although paradoxically, the BrdU LI of the oligodendroglial component is more predictive for survival than the astrocytic component (Wacker et al., 1994) and far advanced tumor progressions are dominated by the astrocytic component.

3. Phenyl N-Tert-Butyl Nitrone (PBN)

A. PBN's

The compound phenyl N-tert-butyl nitrone (PBN) was first synthesized in the 1950's, but in 1968 it was discovered to be very useful to trap and stabilize free radicals in chemical reactions and hence it was termed a spin-trap (Janzen, 1971). Although PBN is the prototype spin-trap, several other nitrones have been synthesized and found useful to trap and characterize free radicals in chemical reactions. These spin traps were used in chemical reactions first, but in the mid-1970's they began to be used to trap free radicals in biochemical and biological systems (Floyd et al., 1977; Poyer et al., 1978). Pharmacokinetic studies have shown that PBN is readily and rapidly distributed almost equally to all tissues, has a half-life in rats of about 132 minutes and is eliminated mostly in the urine. Relatively few metabolism studies have been done, but it is known that some ring hydroxylation (primarily in the para position) of the compound occurs in the liver.

Novelli first showed that PBN could be used to protect experimental animals from septic shock (Novelli et al., 1986), and indeed this was later confirmed by other groups (Pogrebniak et al., 1992). The use of PBN and derivations as pharmacological agents began after discoveries in 1988 that showed that PBN had neuroprotective activity in experimental brain stroke models (Floyd, 1990; Floyd et al., 1996; Carney et al., 1991). These results were repeated and extended, (see Clough-Helfman et al., 1991; Cao et al., 1994; Folbergrova et al., 1995; Pahlmark et al., 1996). Others inventors have summarized the extensive neuroprotective pharmacological research effort on PBN and derivatives (Floyd, 1997; Hensley et al., 1996). In addition to neurodegenerative diseases, PBN has been shown to protect in other pathological conditions where ROS-mediated processes are involved, including diabetes and many other conditions. The mechanistic basis of why PBN and some of its derivatives are so neuroprotective in experimental stroke and several other neurodegenerative models has not been completely elucidated yet. However, it is clear that its action cannot simply be explained by its ability to trap free radicals.

The general formula for PBNs is:

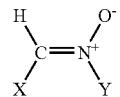

wherein:

X is phenyl or

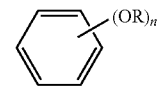

R is H,

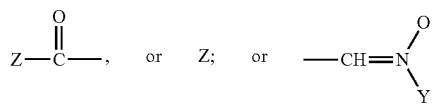

and n is a whole integer from 1 to 5; or

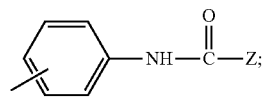

Y is a tert-butyl group that can be hydroxylated or acetylated on one or more positions;
phenyl; or

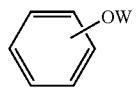

wherein W is

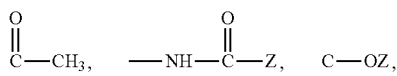

or Z; and Z is a $C_1$ to $C_5$ straight or branched alkyl group.

B. PBN's in Cancer

U.S. Pat. No. 5,569,902 (incorporated herein by reference) describes the use of nitrone free radical trapping agents for the treatment of cancer. Specifically, PBN and related compounds are described as being useful in the preparation of an anti-carcinogenic diet and the preparation of such supplemented diets. Those subjects most likely to beneficially receive the nitrones would include: (1) those having had pretumor tests indicating a high probability of the presence of tumors, (2) those exposed to very potent carcinogenic environments and their probability of tumor progression is high, and (3) to those whose genetic predisposition makes their likelihood of tumor development high.

U.S. Patent Publication 2007/0032453 (incorporated herein by reference) describes the effect of the anti-inflammatory phenyl N-tert-butyl nitrones (PBNs) on gliomas using MRI techniques. PBN itself was able to control tumor development when provided to a subject either before, at the time of or after tumor implantation. Thus, it was proposed to use PBN, and related nitrone free radical trapping agents, as therapeutic agents for gliomas.

C. 2,4-Disulfonyl Phenyl N-Tert-Butyl Nitrone (2,4-Ds-PBN)

U.S. Pat. No. 5,488,145 (incorporated herein by reference) describes 2,4-disulfonyl phenyl-tert-butyl nitrone and its pharmaceutically acceptable salts. These materials were described as useful pharmaceutical agents for oral or intravenous administration to patients suffering from acute central nervous system oxidation as occurs in a stroke or from gradual central nervous system oxidation which can exhibit itself as progressive central nervous system function loss.

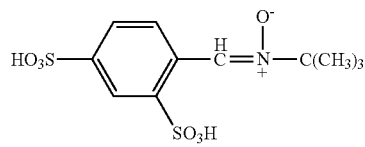

2,4-disulfonyl PBN 2,4-disulfonyl PBN's two sulfonate groups was expected to exhibit improved water solubility, but was also expected to exhibit poor transport across the blood/brain barrier because of its lipophobic character. However, when the present compound was made and tested in vivo, it showed an unexpected increase in efficacy as compared to PBN. This increase in efficacy occurred along with an increase in potency as compared to PBN. In direct contrast to this marked increase in potency and efficacy there was a marked and highly significant decrease in toxicity as compared to PBN.

These results were unexpected because in the general literature on structure/activity relationships within specific defined families of compounds therapeutic potency typically covaries with toxicity. Thus, most related compounds maintain their ratio of therapeutic potency to toxicity. In contrast, the compound of this invention deviates from this expected relationship when its potency increased and its toxicity decreased relative to closely related analogs.

Accordingly, in one aspect, the invention provides the PBN-disulfonyl compound and its pharmaceutically acceptable salts. In a second aspect, the invention provides intravenously- and orally-administrable pharmaceutical compositions having this compound or its salt as active ingredient.

2,4-ds PBN may exists at higher pHs in an ionized salt form:

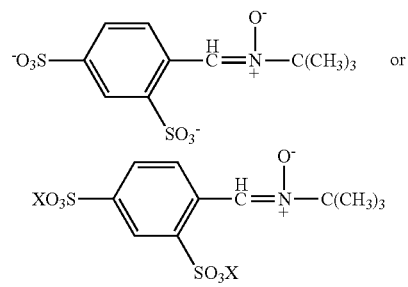

where X is a pharmaceutically acceptable cation. Most commonly, this cation is a monovalent material such as sodium, potassium or ammonium, but it can also be a multivalent alone or cation in combination with a pharmaceutically acceptable monovalent anion, for example calcium with a chloride, bromide, iodide, hydroxyl, nitrate, sulfonate, acetate, tartrate, oxalate, succinate, palmoate or the like anion; magnesium with such anions; zinc with such anions or the like. When these combinations of a polyvalent cation and a monovalent anion are illustrated in structural formulae, herein, the monovalent anion is identified as "Y."

Among these materials, the free acid and the simple sodium, potassium or ammonium salts are most preferred with the calcium and magnesium salts also being preferred but somewhat less so.

2,4-ds PBN can be prepared by a two-step reaction sequence. In the first step, commercially available tertiary butyl nitrate (2-methyl-2-nitropropane) is converted to the corresponding n-hydroxylamine using a suitable catalyst such as an activated zinc/acetic acid catalyst or an aluminum/mercury amalgam catalyst. This reaction can be carried out in 0.5 to 12 hours and especially about 2 to 6 hours or so at a temperature of about 15-100° C. in a liquid reaction medium such as alcohol/water mixture in the case of the zinc catalyst or an ether/water mixture in the case of the aluminum amalgam catalyst.

In the second step, the freshly formed hydroxylamine is reacted with 4-formyl-1,3-benzenedisulfonic acid, typically with a slight excess of the amine being used. This reaction can be carried out at similar temperature conditions. This reaction is generally complete in 10 to 24 hours.

The product so formed is the free acid and is characterized by a molecular weight of 89 g/mole. It is a white powdery material which decomposes upon heating. It is characterized by a solubility in water of greater than 1 gram/ml and a $^1$H NMR spectrum in $D_2O$ of 8.048 ppm (dd, 8.4, 1.7 Hz); 8.836 ppm (d, 8.4 Hz); 8.839 ppm (d, 1.7 Hz); 8.774 ppm (s).

The various salts can be easily formed by admixing the free acid in aqueous medium with two equivalents of the appropriate base, for example, KOH for the potassium salt, and the like.

One synthesis is based on the work by R. H. Hinton and E. G. Janzen (J. Org. Chem. 57:2646-2651, 1992). It involves the condensation of an aldehyde with a hydroxylamine. The hydroxylamine is unstable and is prepared fresh on the day of use using an activated zinc catalyst. The synthesis is as follows.

TABLE 1

Prerequisite Chemicals 1. 95% Ethanol
2. 2-Methyl-2-nitropropane
3. Zinc dust
4. Glacial acetic acid
5. Diethyl ether
6. Saturated sodium chloride
7. Magnesium Sulfate, Anhydrous solid
8. 4-Formyl-1,3-benzenesulfonic acid (MW 310.21 g/mole), disodium salt, hydrate
9. Methanol
10. Dichloromethane

TABLE 2

Preparation of N-t-Butylhydroxylamine

1. A 500 mL three neck round bottom flask is equipped with a magnetic stir bar, thermometer adapter, thermometer, and addition funnel.
2. 95% ethanol (350 mL) was added to the flask and cooled to 10° C. in an ice bath.
3. 2-Methyl-2-nitropropane (6.18 g, 0.060 mole), and zinc dust (5.89 g, 0.090 mole) were added in single portions.
4. Glacial acetic acid (10.8 g, 0.180 mole) was placed in the addition funnel and added dropwise at such a rate with vigorous stirring to maintain the temperature below 15° C.
5. The ice bath was removed and mixture was stirred for 3 hrs at room temperature.
6. The solvent was stripped from the mixture, leaving t-butylhydroxylamine, zinc acetate, and water.
7. Dichloromethane (50 mL) was added and the mixture filtered through a Buchner funnel.
8. The zinc acetate cake left on the filter paper was washed with 2X 25 mL dichloromethane.
9. Water was separated from the filtrate in a separatory funnel and the organic layer dried over magnesium sulfate.
10. The magnesium sulfate was removed by filtering through fluted filter paper, then dichloromethane stripped off by rotary evaporation.
11. The product (100% yield = 5.34 g), viscous liquid, was dissolved in methanol (50 mL) for use below.

TABLE 3

Preparation of 2,4-disulfonylphenyl-N-t-butylnitrone

1. A 3-neck 250 ml round bottom flask was set up with a stir bar, a gas dispersion tube, an addition funnel, and a Friedrichs condenser cooled with recirculating ice water.
2. To the flask were added 200 mL of methanol, 4-formyl-1,3-benzenedisulfonic acid (9.31 g, 30 mmoles) and N-t-butylhydroxylamine (25 mL of the methanol solution from part A, 30 mmoles theoretical).
3. The reaction was heated to reflux with a heating mantle while bubbling the reaction with nitrogen with stirring.
4. The mixture was refluxed for 2 hours.
5. The remainder of hydroxylamine from above was added.

TABLE 3-continued

Preparation of 2,4-disulfonylphenyl-N-t-butylnitrone

6. Refluxing was continued with nitrogen bubbling for at least 18 hours, but not more than 24 hours.
7. The hot reaction mixture was filtered on a Buchner funnel, and the solid washed with hot methanol.
8. The methanol was stripped off by rotary evaporation to a yellow, viscous oil.
9. Hot 1:1 ethanol:acetone (200 mL) was added and the mixture heated to dissolve the oil.
10. The solution was cooled to crystallize the product.
11. The product was collected on a Buchner funnel and dried under vacuum overnight.
12. The reaction typically gives 75% yield of I, a white powder.

Other methods of synthesis are disclosed in the prior art as well.

4. Combination Treatments

In one embodiment, 2,4-ds-PBN may be used in conjunction with another glioma therapy, such as radiation, PCV, DFMO, CCNU or BCNU. These compositions would be provided in a combined amount effective to kill or inhibit proliferation of the cell. This process may involve contacting the cells with the agents at the same time. This may be achieved by contacting the cell with a single composition or pharmacological formulation that includes both agents, or by contacting the cell with two distinct compositions or formulations, at the same time, wherein one composition includes 2,4-ds-PBN and the other includes the second agent.

Alternatively, the 2,4-ds-PBN therapy may precede or follow the other agent treatment by intervals ranging from minutes to weeks. In embodiments where the other agent and 2,4-ds-PBN are applied separately to the cell, tissue or organism, one would generally ensure that a significant period of time did not expire between the time of each delivery, such that the agents would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Multiple administrations of each agent are contemplated. For example, where the 2,4-ds-PBN therapy is "A" and the secondary agent or therapy is "B," the following are contemplated:

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Patients will be evaluated for neurological changes considered to be independent of tumor and graded using NCI Common Toxicity Criteria (neurotoxicity). Aside from baseline audiometric testing, repeat audiometric testing for ototoxicity is performed at the physician's discretion for patients who had evidence of hearing loss or progression of hearing loss by neurological examination. In addition, blood counts are performed biweekly, and serum creatinine, alkaline phosphatase, bilirubin and alanine amino-transferase tests are performed before each cycle. Doses may be modified during the course of treatment, primarily based on neutrophil and platelet counts (vincristine, lomustine and matulane) or ototoxicity (DFMO). Occasionally, DFMO dose reductions are required for diarrhea.

A. PCV

PCV is a drug combination therapy employing three different agents—a hydrazine derivative, matulane, a nitrosourea, lomustine, and a tubulin interactive agent, vincristine. It has been used in a number of clinical trials, most notably by the inventor in assessing its effect on high-grade glioma and medulloblastoma tumors. The major side-effect observed with PCV was dose-limiting myelotoxicity. Each of the components of PCV is described below.

It should be noted that the present invention could include the use of BCNU rather than of CCNU (lomustine) since both are nitrosoureas. It also is contemplated that one could use CCNU and procarbazine or BCNU and procarbazine, without vincristine, since vincristine is usually considered to be the least active of the drugs in the PCV combination.

Both hydrazines and nitrosoureas are alkylating agents. As a group, alkylating agents form covalent chemical adducts with cellular DNA, RNA and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. In addition to hydrazine and nitrosoureas, alkylating agents include: triazenes such as dacarabzine and temozolomide, nitrogen mustards such as chlorambucil, cyclophosphamide, isofamide, mechlorethamine, melphalan, uracil mustard; aziridine such as thiotepa; methanesulphonate esters such as busulfan; platinum complexes such as cisplatin, carboplatin; bioreductive alkylators, such as mitomycin and altretemine. Any of these compounds may be used together or individually, in combination with the compounds of the present invention.

i. Hydrazine and Triazene Derivatives

Hydrazine and triazene derivatives are similar to nitrosoureas in that they decompose spontaneously or are metabolized to produce alkyl carbonium ions, which alkylate DNA. This class of compounds includes matulane, dacarbazine and temozolomide.

The active ingredient in matulane is Procarbazine Hydrochloride (N-isopropl-alpha-(2-methylhydrazino)-p-toluamide monohydrochloride). It is available from Roche Laboratories, Inc. It was approved in 1969 for treatment of Hodgkins' Disease. The typical form is an oral capsule that contains 50 mg procarbazine as the hydrochloride. Dosages vary depending upon whether procarbazine is being used as a combination drug with other anticancer drugs or as a single therapeutic agent. A suggested guideline per the PDR for single agent use is 100 mg two times daily for 14 days.

The exact mode of actions of matulane is not clear. There is some evidence that the drug acts by inhibition of protein, RNA and DNA synthesis. It is primarily metabolized in the liver and kidneys and appears to be auto-oxidized to the azo derivative with the release of hydrogen peroxide. The azo derivative isomerizes to the hydrazone and, following hydrolysis, splits into a benzylaldehyde derivative and methylhydrazine. The methylhydrazine is further degraded to $CO_2$ and $CH_4$, and possibly hydrazine, whereas the aldehyde is oxidized to acid which is excreted in the urine.

Matulane exhibits monamine oxidase inhibitory activity (MAOI), so a diet that restricts foods which contain high tyramine content should be followed. Drugs to be avoided during therapy include antihistamines, sympathomimetics, barbiturates, narcotics, hypotensive agents or phenothiazines, and ethyl alcohol. Some foods are also to be avoided during procarbazine such as naturally aged cheeses, chocolates, nuts, and bananas as they could theoretically lead to a hypertensive complication in some patients. Also, unacceptable toxicity may occur if matulane is used in patients with impairment of renal and/or hepatic function. Treatment may be curtailed in the event of central nervous system signs or symptoms such as paresthesias, neuropathies or confusion; neutropenia (absolute neutrophil count under 1500/μl), thrombocytopenia (platelets under 100,000/μl), hypersensitivity reaction, ulceraction or persistent spot of soreness around the oral cavity, diarrhea or loose stools, hemorrhage or bleeding tendencies.

Adverse but expected reactions include leukopenia, neutropenia, anemia, and thrombocytopenia. Commonly reported acute side effects are nausea and vomiting during or shortly after dose administration.

ii. Nitrosoureas

Nitrosoureas represent a group of therapeutic alklyating agents. This class of compounds includes lomustine, carmustine, semustine, steptozocin, and nimustine.

(a) Lomustine

Lomustine is a synthetic alkylating agent, also known as CCNU, with the chemical name of 1-(2-chloroethyl)-3-cyclohexyl-1-nitrosourea. It was approved in 1977 for treatment of brain tumors and Hodgkin's Disease. It is available from Bristol Myers Squibb as oral capsule, available in 10 mg, 40 mg and 100 mg forms. Dosages may vary depending upon whether lomustine is being used as a single agent or in a combination in addition to other chemotherapeutic agents. As a single agent in previously untreated patients, the recommended dosages per the PDR is 130 mg as a single oral dose every 6 weeks. Lomustine crosses the blood brain barrier.

It is believed that CCNU alkylates DNA and RNA. It is cross-resistant with other nitrosoureas and some but not all alkylating agents. It may also inhibit several key enzymatic processes by carbamoylation of amino acids in proteins.

The most common and severe toxic side effects are bone marrow suppression leading to thrombocytopenia and leukopenia, which may contribute to bleeding and infections. Bone marrow toxicity is cumulative and thus dosage adjustments must be considered on the basis of the nadir blood counts from prior doses.

(b) Carmustine

Carmustine, also known as BCNU, with the chemical name of N,N'-Bis(2-chloroethyl)-N-nitrosurea, is a nitrosurea alkylating agent approved by the FDA in 1977. Carmustine has ben used for many years for treatment of primary brain tumors and is used for the treatment of gliomas. Carmustine is available from Bristol Meyers Squibb in packages containing vials of 10 mg carmustine and 3 ml sterile diluent for delivered by i.v. injection. As a single agent carmustine is administered at about 150-200 mg/m$^2$ every 6 weeks. In combination regimens, carmustine may be given in does similar to those of lomustine. An alternative mode of delivery is by wafers implanted directly into the tumor site (Gliadel® Wafer).

Potential side effects include bone marrow suppression, anemia, diarrhea, low white blood cell and platelet counts, pulmonary toxicity and swallowing difficulties.

iii. Tubulin Interactive Agents

Tubulin interactive agents interfere with cell division by binding to specific sites on Tubulin, a protein that polymerizes to form cellular microtubules. Microtubules are critical cell structure units. When the interactive agents bind on the protein, the cell cannot properly form microtubules.

Tubulin interactive agents include vincristine and vinblastine, both alkaloids and the taxanes, such as paclitaxel and docetaxel.

Vincristine, is available as Oncovin™ from Eli Lilly & Company and as Vincristine Sulfate from Faulding. Also called vincaleukoblastine, a 22-oxo-, sulfate (1:1) (salt), the salt of an alkaloid obtained from a common flowering herb, the periwinkle plant. It is delivered by intravenous injection. It was approved in 1963 on label for Ewing's Sarcoma, rhabdomyosarcoma, Wilm's Tumor, neuroblastoma, Hodgkin's Disease and leukemia.

The mechanism of action remains under investigation; however, there is an indication that inhibition of microtubule formation in the mitotic spindle, resulting in an arrest of dividing cells at the metaphase state, is involved. The liver is the major excretory organ. Most of an intravenous dose of Vincristine is excreted into the bile after rapid tissue binding. Vincristine does not appear to cross the blood brain barrier.

Vincristine has been reported to reduce blood levels of antiseizure medications and to increase seizure activity. The most common adverse reaction is hair loss. Leukopenia, neuritic pain and constipation occur, but usually for less than 7 days.

B. DFMO

Numerous highly proliferative types of cancer are associated with increased levels of the polyamines putrescine, spermidine, and spermine in tumor tissue and blood and urine of mammals with cancer. Studies have shown that this can be related to increased polyamine synthesis by the rate-limiting enzyme, ornithine decarboxylase (ODC). The pathway for polyamine synthesis begins with L-ornithine. This natural amino acid, although not normally incorporated into proteins, is part of the urea cycle which metabolizes arginine to ornithine and urea. Ornithine is converted by ornithine decarboxylase (ODC) to putrescine and $CO_2$ and is considered to be the rate-limiting step in the production of polyamines. With the addition of propylamine donated from S-adenosylmethionine, putrescine is converted to spermidine. Spermidine is then converted to spermine by spermine synthetase, again in association with the decarboxylation of S-adenosylmethionine. Putrescine, spermidine and spermine represent the three major polyamines in mammalian tissues. Polyamines are found in animal tissues and microorganisms and are known to play an important role in cell growth and proliferation. Although the exact mechanism of the role of the polyamines in cell growth and proliferation is not known, it appears that the polyamines may facilitate macromolecular processes such as DNA, RNA, or protein synthesis. Polyamine levels are known to be high in the testes, ventral prostate, and thymus, in psoriatic skin lesions, and in other cells undergoing rapid growth processes.

It also is well known that the rapid proliferation of tumor tissue is marked by an abnormal elevation of polyamine levels. Hence, the polyamines also may play an important role in the maintenance of tumor growth. Thus, ODC inhibitors, such as DFMO, may exert their therapeutic effect by blocking the formation of the polyamines and thereby slowing, interrupting, or arresting the proliferation and metastases of the tumor tissue.

DFMO (α-difluoromethylornithine, eflornithine, Ornidyl®) is a structural analog of the amino acid L-ornithine and has a chemical formula $C_6H_{12}N_2O_2F_2$. DFMO can be employed in the methods of the invention as a racemic (50/50) mixture of D- and L-enantiomers, or as a mixture of D- and L-isomers where the D-isomer is enriched relative to the L-isomer, for example, 70%, 80%, 90% or more by weight of the D-isomer relative to the L-isomer. The DFMO employed may also be substantially free of the L-enantiomer.

The dose limiting toxic effect of DFMO is thrombocytopenia (abnormally few platelets in the blood), which occurs in about 50% of patients, leukopenia (abnormally few leukocytes), or anemia. This toxic effect is relatively harmless and reversible and cease upon withdrawal of the drug.

The effect of an ODC inhibitor for the control of the growth rate of rapidly proliferating tumor tissue has been assessed in standard animal tumor models. For example, the anti-tumor effect of DFMO has been demonstrated in the following animal tumor models: L1210 leukemia in mice, EMT6 tumor in Balb/C mice, 7,12-dimethylbenzanthracene-induced (DMBA-induced) mammary tumor in rats, and DFMO Morris 7288C or 5123 hepatoma in Buffalo rats. In addition, the anti-tumor effect of DFMO in combination with various cytotoxic agents has been demonstrated as follows: (a) in combination with vindesine or adriamycin in L1210 leukemia in mice, in Morris 7288C hepatoma in Buffalo rats, and in EMT6 tumor in mice, (b) in combination with cytosine arabinoside in L1210 leukemia in mice, (c) in combination with methotrexate in L1210 leukemia in mice, (d) in combination with cyclophosphamide in EMT6 tumor in mice and in DMBA-induced tumor in mice, (e) in combination with BCNU in mouse glioma 26 brain tumor, and (f) in combination with MGBG in L1210 leukemia in mice, in Morris 7288C hepatoma in Buffalo rats, in P388 lymphocytic leukemia in mice, and in S-180 sarcoma in mice.

Although DFMO can effectively block tumor putrescine biosynthesis, the resultant antitumor effect is cytostasis, not cytotoxicity. For example, DFMO reduces the growth rate of an MCA sarcoma, but does not produce tumor regression. This finding is consistent with reports of other investigators who showed that DFMO is a cytostatic agent. However, studies indicate that a significant role may exist for DFMO agents, permitting the future development of combination chemotherapeutic regimens which incorporate DFMO.

The initial promise of DFMO as a therapeutic ODC inhibitor for use in the treatment of various neoplasias has dimmed somewhat because, although DFMO does, in fact, irreversibly inhibit ODC activity, cells treated in vivo with DFMO significantly increase their uptake of exogenous putrescine as described in U.S. Pat. No. 4,925,835. The intercellular transport mechanisms of the cell do an "end run" around the DFMO-impaired ODC activity by importing putrescine from the extracellular milieu. Therefore, DFMO's effect in vivo is far poorer than in vitro. So, while DFMO treatment effectively inhibits intracellular putrescine neogenesis, it also results in increased uptake of extracellular putrescine, thereby offsetting its ODC inhibitory effect.

This problem is compounded by the fact that putrescine is present in many common foods, such as grapefruit juice, which contains approximately 400 ppm putrescine. This makes it virtually impossible to provide a patient a nutritionally sufficient diet which is free of putrescine. Therefore, DFMO-treated cells are capable of importing sufficient amounts of extracellular putrescine to support cell division.

Strategies to make DFMO more acceptable to human patients are described in U.S. Pat. No. 4,859,452 (incorporated by reference). Formulations of DFMO are described which include essential amino acids in combination with either arginine or ornithine to help reduce DFMO-induced toxicities.

C. Radiation

Factors that cause DNA damage and have been used extensively for cancer therapy and include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

D. Surgery

Approximately 60% of persons with cancer will undergo surgery of some type, which includes preventative, diagnostic or staging, curative and palliative surgery. Curative surgery as a cancer treatment may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

5. Pharmaceutical Formulations

The present invention discloses numerous compositions, which in certain aspects of the invention, are administered to animals. For example, 2,4-ds-PBN, as well as various secondary chemotherapeutic agents, will be formulated for administration. Where clinical applications are contemplated, it will be necessary to prepare pharmaceutical compositions of these compounds and compositions in a form appropriate for the intended application. Generally, this will entail preparing compositions that are essentially free of pyrogens, as well as other impurities that could be harmful to humans or animals.

One will generally desire to employ appropriate salts and buffers to render agents suitable for introduction into a patient. Aqueous compositions of the present invention comprise an effective amount of the agent, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients, such as other anti-cancer agents, can also be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

An effective amount of the agents is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

A. Enteral Administration

The active compounds of the present invention can advantageously be formulated for enteral administration, e.g., formulated for oral administration. The pharmaceutical forms may include sesame oil, peanut oil or aqueous propylene glycol; and sterile powders for the extemporaneous preparation of ingestible compositions, including tables, pills and capsules. Also, it is contemplated that the agents of the present invention can be provided in the form of a food additive and incorporated into a daily dietary program. All of these forms are generally selected to be sterile and stable under the conditions of manufacture and storage.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the particular methods of preparation are vacuum-drying and freeze-drying techniques which yield a powder of the active ingredient plus any additional desired ingredient from a previously sterile-filtered solution thereof.

B. Other Routes of Administration

In addition to the compounds formulated for enteral administration, parenteral formulations such as intravenous or intramuscular injection are envisioned. Administration may also be nasal, buccal, rectal, vaginal or topical. Alternatively, administration may be by intradermal, subcutaneous, or intraperitoneal injection. Also contemplated is continuous perfusion via catheter. Such compositions would normally be administered as pharmaceutically acceptable compositions, described supra.

6. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute specifically contemplated modes for its practice. However, those of skill in the art should, in light of the present disclosure, appreciate that many changes can be made in the specific embodiments which are disclosed and still obtain a like or similar result without departing from the spirit and scope of the invention.

Example 1

The inventors used an intracerebral C6 rat glioma cell implantation method, widely accepted by the glioma research field, as a good model for gliomas. To induce glioma in rats, C6 rat glioma cells ($10^6$ cells in 10 µL were injected into the cerebral cortex of male Fischer 344 rats. Fifteen days later, 2,4-ds-PBN was orally administered through drinking water (0.015%, 17.5 mg/kg). The efficacy of 2,4-ds-PBN was assessed with the tumor growth patterns and growth rates by using magnetic resonance (MR) imaging (T1/T2-weighted imaging) methods over the course of a month.

FIGS. 1A-C show an example of the progressive development of a rat glioma at 10 (FIG. 1A), 15 (FIG. 1B) and 18 (FIG. 1C) days after intracerebral implantation of C6 rat glioma cells. Histological evaluations were also done for the C6 rat glioma model. FIGS. 2-1(a)-2-2(c) show representative histological slides from regions associated with the glioma and comparative control tissue in the contralateral side. Immunohistochemistry data for the von Willebrand factor indicates endothelial cell proliferation is present in the necrotic centers (FIG. 2-2c), and small blood vessels are revealed in other parts of the glioma (FIG. 2-2b), whereas there is no presence of new vasculature in the control side (FIG. 2-2a), indicating that angiogenesis associated with glioma formation is present.

Figure 4:
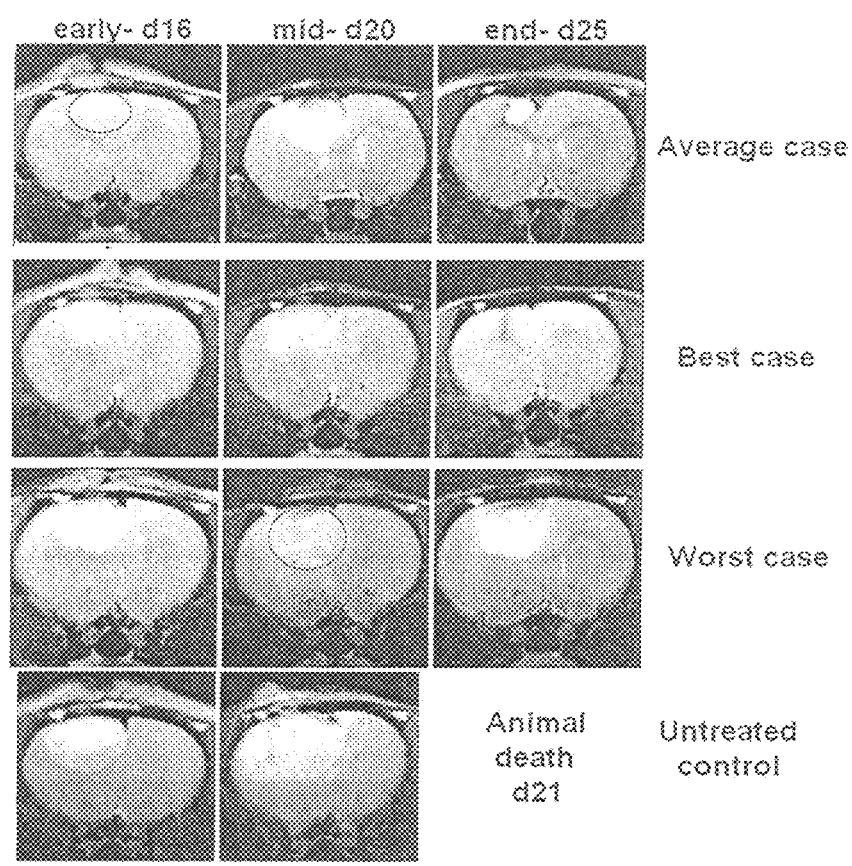
FIG. 4: MR images of 2,4-ds-PBN- and non-treated rats with C6 gliomas (post-tumor>15 days). Tumors are hyperintense regions (outlined). Images at day 16 (d16), d20 and d25.
Figure 5:
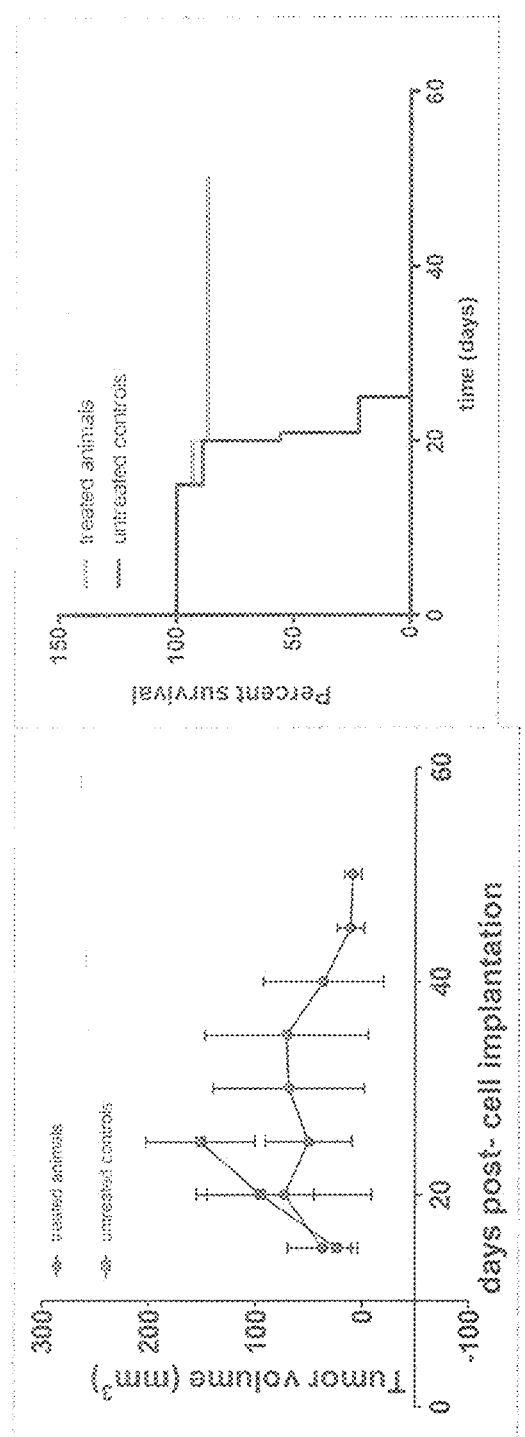
FIG. 5: (Left panel) Tumor volumes measured from MR images of rats with C6 gliomas treated with 2,4-ds-PBN (18 mg/kg/day in drinking water) compared to untreated rats. (Right panel) Percent survival of rats with C6 gliomas treated with 2,4-ds-PBN compared to untreated rats.
Figure 6:
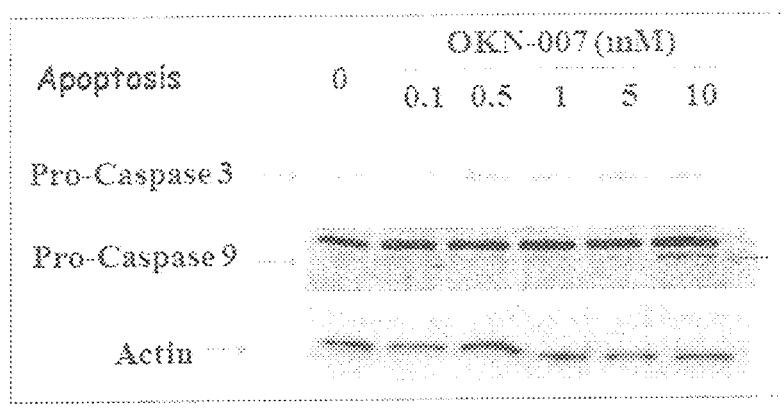
FIG. 6: Western blots of rat C6 cells with increasing concentrations of 2,4-ds-PBN. Increasing levels of apoptotic factors pro-caspase 3 and pro-caspase 9 are shown, relative to actin.

FIG. 4 represents a series of MR images taken over a period of 25 days for an untreated control group and representative data (best-case, average effect, and worst-case) for 2,4-ds-PBN-treated rats (via drinking water administration at a dose of 17 mg/kg/day). The 2,4-ds-PBN studies indicated that a similar effect was observed as seen for PBN, where the C6 glioma tumor volumes were significantly decreased (>15-fold decrease; n=15 for 2,4-ds-PBN-treated rats, and n=5 for non-treated rats) in 2,4-ds-PBN-treated rats (see FIG. 5). Rats treated with 2,4-ds-PBN achieved >80% survival over the 40 day study period (n=15), compared to non-treated rats (n=5). No side effects were observed during the treatment period. Gross signs of adverse effects that were monitored included weight loss, ruffling of fur, and behavioural and postural changes. No toxicity effects were detected (gross examination of tissues/organs during necropsies and histological assessment). FIG. 6 illustrates one of the possible mechanisms of 2,4-ds-PBN, where in C6 cells, it is found to be pro-apoptotic as concentration increases.

However, studies also showed that PBN significantly inhibited cell proliferation in a concentration dependent manner, but by contrast, 2,4-ds-PBN and S-PBN showed little effect. The inventors then examined iNOS and VEGF protein expressions in the 2,4-ds-PBN treated C6 cells. 2,4-ds-PBN (100 µM) treatment significantly lowered the iNOS expression (approximately 75% decrease) as compared with PBN (5% decrease at 100 µM), and VEGF expression was reduced by 50% when cells were treated with 5 mM 2,4-ds-PBN. These results suggest that tumor suppression by 2,4-ds-PBN depends on decreased angiogenesis, decreased iNOS, as well as increased apoptosis rather than cell growth inhibition. The effect of each nitrone compound in cells showed the same tendency as in the rat model, suggesting that the cellular model may replicate in vivo tumor regression mechanism in this model. From these studies, it can be concluded that 2,4-ds-PBN significantly decreases tumor volumes as well as increases subject survivability.

* * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Publication 2007/0032453
U.S. Pat. No. 5,569,902

U.S. Pat. No. 5,488,145
Bigner et al., *In: Pathology of Tumors of the Nervous System*, Russell and Rubinstein (Eds.), 6th Edition, London:Edward Arnold, 757, 1998.
Burger et al., *In: Surgical Pathology of the Nervous System and Its Coverings*, 3$^{rd}$ ed., New York, Churchill Livingstone, Inc, 737, 1991.
Burger et al., *Cancer*, 56:1106-1111, 1985.
Burger et al., *Cancer*, 59:1345-1352, 1987.
Cao et al., *Brain Res.*, 644:267-272, 1994.
Cao et al., *J. Clin. Oncol.* 23:4127-36, 2005.
Carney et al., *Proc. Natl. Acad. Sci. USA*, 88:3633-3636, 1991.
Clough-Helfman et al., *Free Radic. Res. Commun.*, 15:177-186, 1991.
Daumas-Duport et al., *J. Neurooncol.*, 34:61-78, 1997.
Davis et al., *J. Neurooncol.*, 24:9-12, 1995.
Dehghani et al., *Acta Neuropathol.*, 95:493-504, 1998.
Dimova et al., *Thromb. Haemost.*, 93:1176-1184, 2005.
Doblas et al., *Free Radic. Biol. Med.* 44:63-72, 2008.
Ernestus et al., *Acta. Histochem. Suppl.*, 42:159-164, 1992.
Ernestus et al., *J. Neurooncol.*, 29(2):167-174, 1996.
Floyd et al., *FASEB J.*, 4:2587-2597, 1990.
Floyd et al., In: *Neuroprotective Approaches to the Treatment of Parkinson's Disease and other Neurodegenerative Disorders*, Chapman et al. (Eds.), Academic Press Limited, London, 69-90, 1996.
Floyd, *Adv. Pharmacol.*, 38:361-378, 1997.
Folbergrova et al., *Proc. Natl. Acad. Sci. USA*, 92:5057-5061, 1995.
Heegard et al., *Cancer*, 76:1809-1813, 1995.
Hensley et al., In: *Neuroprotective Agents and Cerebral Ischaemia*, Green and Cross (Eds.), Academic press Ltd., London, 299-317, 1996.
Hoshino et al., *Int. J. Cancer*, 53:550-555, 1993.
Kleihues and Cavenee, In: *Pathology and Genetics of Tumors of the Nervous System*, IARC Press, Lyon, 227-228, 2000.
Kleihues and Ohgaki, *Brain Pathol*, 7:1131-1136, 1997.
Kleihues and Ohgaki, *Neuro-Oncology*, 1:44-51, 1999.
Kleihues et al., In: *Histological Typing of Tumours of the Central Nervous System*, 2$^{nd}$ Ed., Berlin: Springer-Verlag, 112, 1993.
Kros et al., *Cancer*, 78:1107-1113, 1996.
Lamborn et al., *Cancer*, 85:925-935, 1999.
Levin and Prados, *J. Clin. Oncol.*, 10(5):766-71, 1992.
Levin et al., *Clin. Cancer Res.*, 6(10):3878-3884, 2000.
Levin et al., *Int. J. Radiat. Oncol. Biol. Phys.*, 32(1):75-83, 1995.
Muller et al., *Acta Neurochir (Wien)*, 37:75-91, 1977.
Pahlmark et al., *Acta Physiol. Scand.*, 157:41-51, 1996.
Pogrebniak et al., *Surgery*, 112:130-139, 1992.
Poyer et al., *Biochim. Biophys. Acta*, 539:402-409, 1978.
Prados et al., *Neurosurgery*, 24(6):806-809, 1989.
Scalabrino and Ferioli, *Cancer Detect. Prev.*, 8(1-2):11-16, 1985.
Scalabrino et al., *J. Natl. Cancer Inst.*, 68(5):751-754, 1982.
Schneider et al., *Acta Neuropathol* 107:272-6, 2004.
Shaw et al., *Neurosurgery*, 34:577-582, 1994.
Shuaib et al., *N. Engl. J. Med.* 357:562-71, 2007.
Wacker et al., *J. Neuro-Oncology*, 19:113-122, 1994.
Wang and Shuaib, *Drugs Aging* 24:537-46, 2007.
Wang et al., *Proc. Natl. Acad. Sci. USA*, 92:5510-5514, 1995.

The invention claimed is:

1. A method for treating glioma recurrence comprising administering to a subject previously having a glioma a dose of 2,4-disulfonyl phenyl tert-butyl nitrone (2,4-ds-PBN) sufficient to treat recurrence of said glioma.

2. The method of claim 1, wherein administration is through a route requiring subsequent passage of 2,4-ds-PBN across said subject's blood brain barrier.

3. The method of claim 2, wherein the route is enteral, intravenous, or intaarterial.

4. The method of claim 1, wherein said glioma is an astrocytoma, an oligodendroglioma, or a glioblastoma multiforme.

5. The method of claim 1, wherein the effective dose is from about 5 to about 150 mg/kg body weight per day.

6. The method of claim 1, further comprising administering a second agent that treats glioma recurrence.

7. The method of claim 1, further comprising screening for glioma recurrence in said subject.

8. The method of claim 1, wherein enteral administration is through dietary supplementation of a food component.

9. The method of claim 8, wherein the effective amount is from about 0.005 w/w % to about 0.1 w/w % of the diet being administered.

10. The method of claim 1, wherein the enteral administration is in the form of a pill or a liquid.

11. The method of claim 1, wherein the subject has previously failed one or more anti-glioma therapies.

12. The method of claim 1, wherein the subject is a human subject.

* * * * *

UNITED STATES PATENT AND TRADEMARK OFFICE
CERTIFICATE OF CORRECTION

| | |
|---|---|
| PATENT NO. | : 9,474,748 B2 |
| APPLICATION NO. | : 14/159753 |
| DATED | : October 25, 2016 |
| INVENTOR(S) | : Rheal A. Towner and Robert A. Floyd |

It is certified that error appears in the above-identified patent and that said Letters Patent is hereby corrected as shown below:

In the Specification

Column 1, beginning on Line 11, insert:
--This invention was made with government support under grant number P20RR016478 awarded by the National Institutes of Health. The government has certain rights in the invention.--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*